US006821983B2

(12) United States Patent
Su et al.

(10) Patent No.: US 6,821,983 B2
(45) Date of Patent: Nov. 23, 2004

(54) 5-(9-ACRIDINYLAMINO)-TOLUIDINE COMPOUNDS

(75) Inventors: Tsann-Long Su, Taipei (TW); Jang-Yang Chang, Taipei (TW); Ting-Chao Chou, Paramus, NJ (US)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 10/630,343

(22) Filed: Jul. 30, 2003

(65) Prior Publication Data

US 2004/0198765 A1 Oct. 7, 2004

Related U.S. Application Data

(60) Provisional application No. 60/460,311, filed on Apr. 4, 2003.

(51) Int. Cl.$^7$ ..................... A61K 31/473; C07D 219/08
(52) U.S. Cl. ...................... 514/297; 546/106; 546/105; 546/103
(58) Field of Search ......................... 514/297; 546/106, 546/105, 103

(56) References Cited

U.S. PATENT DOCUMENTS

| 5,354,864 A | 10/1994 | Watanabe et al. ........... 546/106 |
| 5,939,428 A | 8/1999 | Su et al. ..................... 514/297 |

OTHER PUBLICATIONS

Zaimen A. Arlin, "Current Status of Amsacrine (AMSA) Combination Chemotherapy Programs in Acute Leukemia", *Cancer Treatment Reports*, vol. 67, No. 11, pp. 967–970 (Nov. 1983).
Bruce C. Baguley, et al., "Potential Antitumor Agents. 34. Quantitative Relationships between DNA Binding and Molecular Structure for 9–Anilinoacridines Substituted in the Anilino Ring", *J. Med. Chem.*, vol. 24, pp. 170–177 (1981).
Bruce C. Baguley, et al., "Synthesis, Antitumor Activity, and DNA Binding Properties of a New Derivative of Amsacrine, N–5–Dimethyl–9–[(2–methoxy–4–methylsulfonylamino) phenylamino]–4–acridinecarboxamide[1,2]", *Cancer Research*, vol. 44, pp. 3245–3251 (Aug., 1984).
B.F. Cain et al., "The Experimental Antitumour Properties of Three Congeners of the Acridylmethanesulphonanilides (AMSA) Series" *European Journal of Cancer*, vol. 10, No. 8, pp. 539–549 (Aug. 1974).
Bruce F. Cain et al., "Potential Antitumor Agents. 16. 4'–(Acridin–9–ylamino) methanesulfonanilides", *Journal of Medicinal Chemistry*, vol. 18, No. 11, pp. 1110–1117 (1975).

Bruce F. Cain et al., "Potential Antitumor Agents. 14. Acridylmethanesulfonanilides", *Journal of Medicinal Chemistry*, vol. 17, No. 9, pp. 922–930 (1974).
William A. Denny et al., "Potential Antitumor Agents. 36. Quantitative Relationships between Experimental Anittumor Activity, Toxicity, and Structure for the General Class of 9–Anilinoacridine Antitumor Agents", *J. Med. Chem.*, vol. 25, pp. 276–315 (1982).
Gordon W. Rewcastle et al., "Potential Antitumor Agents. 46. Structure–Activity Relationships for Acridine Monosubstituted Derivatives of the Antitumor Agent N–[2–(Dimethylamino)ethyl]–9–aminoacridine–4–carboxamide", *J. Med. Chem.*, vol. 29, pp. 472–477 (1986).
I. G. C. Robertson et al., "Differences in the metabolism of the antitumour agents amsacrine and its derivative CI–921 in rat and mouse", *Xenobiotica*, vol. 22, No. 6, pp. 657–669 (1992).
I. G. C. Robertson et al., "Involvement of Glutathione in the Metabolism of the Anilinoacridine Antitumour Agents CI–921 and Amsacrine", *Drug Metabolism and Drug Interactions*, vol. VI, No. 3–4, pp. 371–381 (1988).
T. D. Sakore et al., "Visualization of Drug–Nucleic Acid Interactions at Atomic Resolution", *J. Mol. Biol.*, vol. 135, pp. 763–785 (1979).
D.D. Shoemaker et al., "Identification of the Principal Biliary Metabolite of 4'–(9–Acridinylamino)Methanesulfon–m–Anisidide in Rats", *Drug Metabolism and Disposition*, vol. 10, No. 1, pp. 35–39 (Jan./Feb. 1982).
D. D. Shoemaker et al., "Metabolism of 4' –(9–Acridinylamino)methanesulfon–m–anisidide by Rat Liver Microsomes", *Cancer Research*, vol. 44, pp. 1939–1945 (May 1984).
Su et al., "A new class of water soluble acridinyl derivatives that exhibit Topo II mediated DNA cleavage and antitumor efficacy", *Am. Cancer Res.*, 368, 2190 (1994) from the abstract book of the 85th meeting of the American Association for Cancer Research (Apr. 10–13, 1994).
Su et al., "9–Substituted Acridine Derivatives and Long Half–Life and Potent Antitumor Activity: Synthesis and Structure—Activity Relationships", *J. Med. Chem.*, vol. 38, pp. 3226–3235 (1995).
Su et al., "Synthesis and Structure—Activity Relationships of Potential Anticancer Agents: Alkylcarbamates of 3–(9–Acridinylamino)–5–hydroxymethylaniline", *J. Med. Chem.*, vol. 42, pp. 4741–4748 (1999).
Su et al., "Development of 3–(9–Acridinylamino)–5–hydroxymethyl–anilines as Potential Topoisomerase II–Mediated Anticancer Agents", *Cancer Detect. Prev. 2000/Suppl.*, vol. 24, pp. 211(2000).

*Primary Examiner*—Charanjit S. Aulakh
(74) *Attorney, Agent, or Firm*—Fish & Richardson P.C.

(57) ABSTRACT

This invention relates to 9-anilinoacridine compounds, and more particularly to their synthesis and their use in pharmaceutical compositions for treating diseases.

35 Claims, No Drawings

5-(9-ACRIDINYLAMINO)-TOLUIDINE COMPOUNDS

CROSS REFERENCE TO RELATED APPLICATIONS

This application claims the benefit of prior U.S. provisional application 60/460,311, filed Apr. 4, 2003, which is incorporated in its entirety herein by reference.

TECHNICAL FIELD

This invention relates to 9-anilinoacridine compounds, and more particularly to their synthesis and their use in pharmaceutical compositions for treating diseases.

BACKGROUND

Inhibitors of topoisomerase II can exhibit antitumor activity. Among such inhibitors are 9-anilinoacridine compounds, e.g., 4'-(9-acridinylamino) methanesulfon-m-anisidine (m-AMSA) and CI-921 (5-methyl-4-methylcarboxamide derivative of m-AMSA), both of which were investigated for the treatment of leukemia and solid tumors. See e.g., Cain et al., Eur. J. Cancer 1974, 10:539 and Arlin Z., *Cancer Treat. Rep.* 1983, 967 and Baguley et al., *Cancer Res.* 1984, 44:3245 and Denny et al., *J. Med. Chem.* 1987, 30:658. A distinguishing chemical feature of these two 9-anilinoacridines is that they can readily undergo reversible oxidation, chemically or microsomally, to give quinonediimines. See e.g., Shoemaker et al, *Cancer Res.* 1984, 44:1939 and Shoemaker et al., *Drug Metab. Dispos.* 1982, 10:35.

Su et al. reported a series of 9-anilinoacridines that exhibited antitumor activity, but were incapable of quinonediimine formation. See e.g., Su et al. *Am. Assoc. Cancer Res.* 1994, 368, U.S. Pat. No. 5,939,428, *J. Med. Chem.* 1995, 38, 3226–3235; and *J. Med. Chem.* 1999, 42, 4147–4748. Examples include derivatives in which the 9-amino group was substituted by an oxygen or sulfur atom, and those in which the aniline substituents were located meta to the nitrogen attached to the 9-position of the acridine ring. Among the latter compounds, a series of 3-(acridin-9-yl)amino-5-hydroxymethylanilines and their ethylcarbamate derivatives were shown to have significant antitumor activity both in vitro and in vivo.

SUMMARY

In one aspect, this invention features compounds of Formula (I):

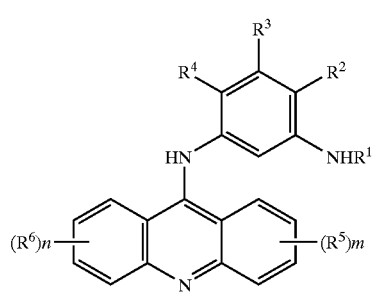

(I)

In the above formula, $R^1$ is hydrogen, $COR^a$, or $COOR^a$; each of $R^2$, $R^3$ and $R^4$ is, independently, hydrogen, $C_1$–$C_{10}$ alkyl, or $OR^b$, with the proviso that $R^2$, $R^3$ and $R^4$ cannot all be hydrogen. Each of $R^5$ and $R^6$ is, independently, hydrogen, $C_1$–$C_6$ alkyl, $OR^c$, nitro, halo, $N(R^c)_2$, $NH(CH_2)_pN(R^c)_2$, $(CH_2)_qOH$, $(CH_2)_qX$, $CONHR^c$, $CONH(CH_2)_pN(R^c)_2$, $SO_3R^c$, or $SO_2R^c$ with the proviso that when $R^1$ is hydrogen and $R^4$ is $CH_3$, $R^5$ and $R^6$ cannot both be hydrogen. Each of m and n, is independently, 0–4. $R^a$ is aryl, or $C_1$–$C_{10}$ alkyl, optionally substituted with oxo; $R^b$ is $C_1$–$C_{10}$ alkyl; $R^c$ is hydrogen or $C_1$–$C_{10}$ alkyl; p is 1–5; and q is 1–3.

Referring to formula (I) above, a subset of the compounds described above are those in which one of $R^2$, $R^3$ and $R^4$ is $C_1$–$C_6$ alkyl or $OR^b$ and one of $R^2$, $R^3$ and $R^4$ is hydrogen. $R^2$, $R^3$, $R^4$ and $R^b$ can be $C_1$–$C_4$ alkyl. $R^2$, $R^3$ and $R^4$ and $OR^b$ can be e.g., $CH_3$ or $OCH_3$.

Embodiments can include one or more of the following.

$R^1$ can be hydrogen, $COR^a$ or $COOR^a$, and $R^a$ can be $C_1$–$C_4$ alkyl, optionally substituted with oxo (e.g., $R^1$ can be $COCH_2CH_2COCH_3$ or $COOCH_2CH_3$).

Each of $R^5$ and $R^6$ can be independently, hydrogen, $C_1$–$C_6$ alkyl, $OR^c$ or $CONHR^c$, or $CONH(CH_2)_pN(R^c)_2$ and each of m and n can be, independently, 1. $R^c$ can be $C_1$–$C_4$ alkyl, and p can be 2. $R^5$ and $R^6$ can occupy the C-4 and C-5 positions of the acridine ring, respectively. For example, $R^5$ can be $CONH(CH_2)_2N(CH_3)_2$ and $R^6$ can be $CH_3$.

The compound can be {3-[4-(2-dimethylamino-ethylcarbamoyl)-5-methyl-acridin-9-ylamino]-5-methyl-phenyl}-carbamic acid ethyl ester.

The compound can be {3-[4-(2-dimethylamino-ethylcarbamoyl)-5-methyl-acridin-9-ylamino]-4-methyl-phenyl}-carbamic acid ethyl ester.

The compound can be [9-(3-amino-5-methyl-phenyl)amino]-5-methyl-acridine-4-carboxylic acid (2-dimethylamino-ethyl)-amide.

The compound can be [9-(5-amino-4-methyl-phenyl)amino]-5-methyl-acridine-4-carboxylic acid (2-dimethylamino-ethyl)-amide.

The term "halo" refers to any radical of fluorine, chlorine, bromine and iodine. The term "alkyl" refers to both cyclic and acyclic, saturated and unsaturated non-aromatic $C_1$–$C_{10}$ hydrocarbon moieties, e.g., $CH_3$, $CH=C_2H_4$, or $C_6H_{11}$ (cyclic). The term "haloalkyl" refers to an alkyl in which one or more hydrogen atoms are replaced by halo, and includes alkyl moieties in which all hydrogens have been replaced by halo (e.g., perfluoroalkyl). The term "aryl" refers to both hydrocarbon aryl moieties and heteroaryl moieties. Examples of hydrocarbon aryl moieties include phenyl, naphthyl, pyrenyl, anthryl, and phenanthryl. Examples of heteroaryl moieties include furyl, fluorenyl, pyrrolyl, thienyl, oxazolyl, imidazolyl, thiazolyl, pyridyl, pyrimidinyl, quinazolinyl, and indolyl.

The term "oxo" refers to an oxygen atom, which forms a carbonyl when attached to carbon.

Shown below are exemplary compounds, compounds 1–12, of this invention:

1
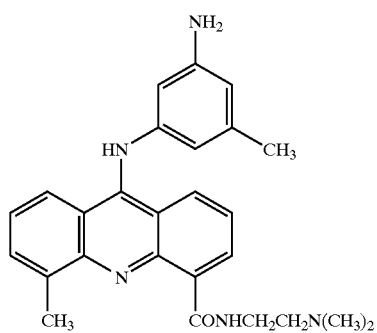
2
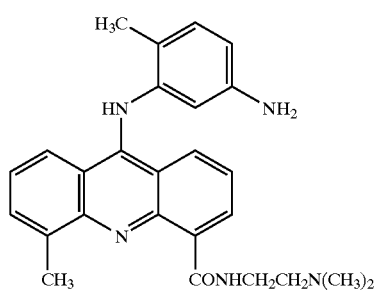
3
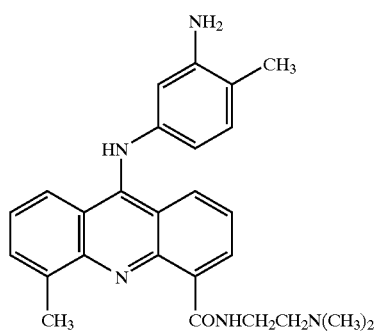
4
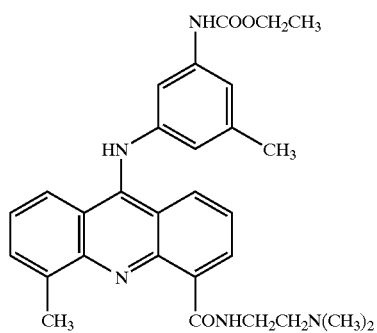
5
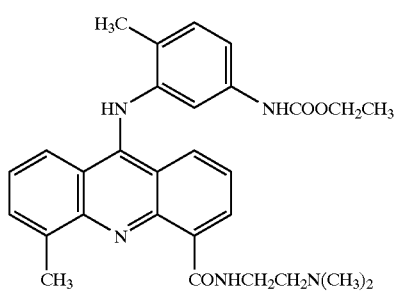
-continued
6
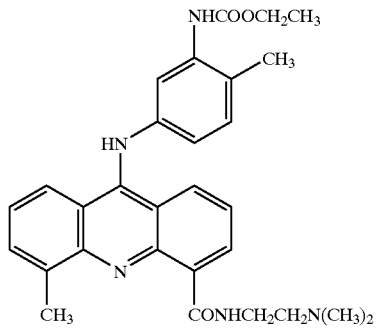
7
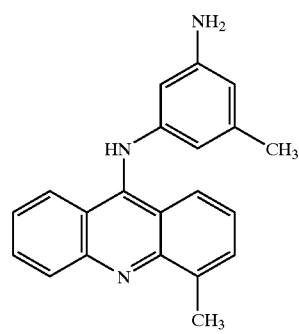
8
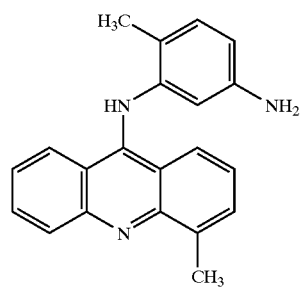
9
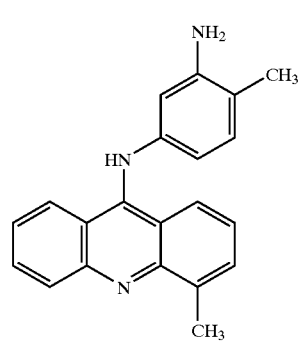
10
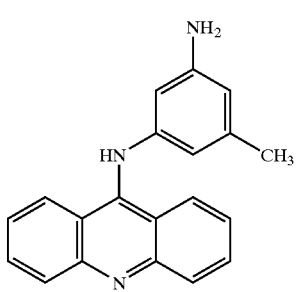

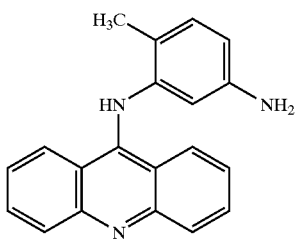

11

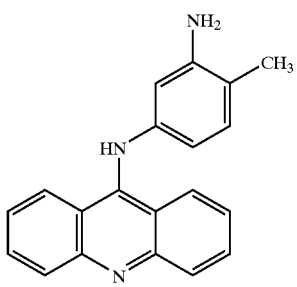

12

The 9-anilinoacridine compounds of this invention include the compounds themselves, as well as their salts and their prodrugs, if applicable. A salt, for example, can be formed between an anion and a positively charged substituent (e.g., amino) on a 9-anilinoacridine compound. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., sulfate) on a 9-anilinoacridine compound of this invention. Suitable cations include sodium ion, potassium ion, magnesium ion, calcium ion, and an ammonium cation such as tetramethylanunonium ion. Examples of prodrugs include esters and other pharmaceutically acceptable derivatives, which, upon administration to a subject, are capable of providing active 9-anilinoacridine compounds.

In another aspect, the invention features a pharmaceutical composition that contains an effective amount of at least one of the 9-anilinoacridines described above and a pharmaceutically acceptable carrier. Also within the scope of this invention is a composition containing one or more of the 9-anilinoacridine compounds described above for use in treating cancer, and the use of such a composition for the manufacture of a medicament for the just-mentioned use.

In still another aspect, the invention is a method of treating a subject (e.g., human, mammal, dog, cat, horse) having cancer including administering to the subject an effective amount of a compound of Formula (I). The cancer can be a human leukemia, sarcoma, osteosarcoma, lymphoma, melanoma, ovarian, skin, testicular, gastric, pancreatic, renal, breast, prostate colorectal, head and neck, brain, esophageal, bladder, adrenal cortical, lung, bronchus, endometrial, cervical or hepatic cancer.

In one aspect, the invention features a method for synthesizing a compound of Formula (II):

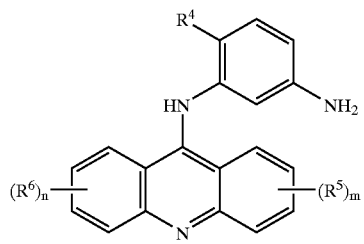

(II)

The method includes contacting a compound of Formula (III):

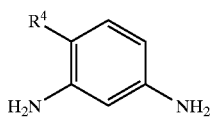

(III)

with a compound of Formula (IV):

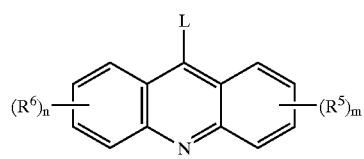

(IV)

to form a compound of Formula (II). $R^4$ is $C_1$–$C_{10}$ alkyl or $OR^b$. Each of $R^5$ and $R^6$ is, independently, hydrogen, $C_1$–$C_6$ alkyl, $OR^c$, nitro, halo, $N(R^c)_2$, $NH(CH_2)_pN(R^c)_2$, $(CH_2)_qOH$, $(CH_2)_qX$, $CONHR^c$, $CONH(CH_2)_pN(R^c)_2$, $SO_3R^c$, or $SO_2R^c$. Each of m and n, is independently, 0–4. $R^a$ is aryl, or $C_1$–$C_{10}$ alkyl, optionally substituted with oxo; $R^b$ is $C_1$–$C_{10}$ alkyl; $R^c$ is hydrogen or $C_1$–$C_{10}$ alkyl; p is 1–5; q is 1–3; L is halo, $OSO_2R^7$, or $OR^7$; and $R^7$ is alkyl, haloalkyl, or aryl optionally substituted with halo or nitro.

The details of one or more embodiments of the invention are set forth in the description below. Other features, objects, and advantages of the invention will be apparent from the description and from the claims.

DETAILED DESCRIPTION

The compounds of this invention can be synthesized using conventional techniques. Advantageously, these compounds are conveniently synthesized from readily available starting materials. In general, the compounds of the formulae described herein are conveniently obtained via standard organic chemistry synthesis methods, including those methods illustrated in the schemes and the examples herein.

SCHEME 1

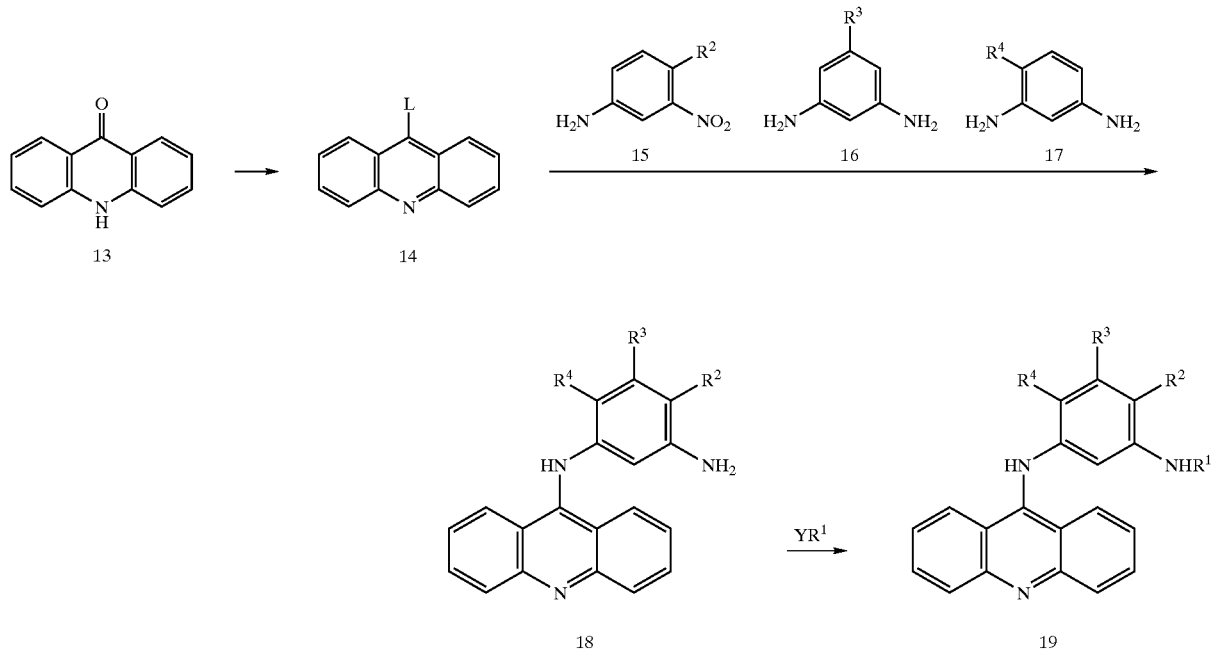

$R^1$ is $COR^3$ or $COOR^3$

An exemplary scheme of synthesizing the 9-anilinoacridines of this invention is presented above (for definitions of $R^2$, $R^3$, $R^4$, and $R^a$, see Formula I). 9-Acridone 13 can be converted to compound 14, which contains a leaving group "L" at the 9-position. The leaving group may be halo, triflate, mesylate, nosylate or phenoxy. Preferably, L is chloro. Acridine 18 can be obtained via the condensation of diamines 16 or 17 with 14. In the case of the symmetrical diamine 16, nucleophilic displacement of "L" by either amino group can afford 9-anilinoacridines in which the substituent $R^3$ is meta to the nitrogen attached to the acridine ring (e.g., 1, 4, 7 and 10). On the other hand, the unsymmetrical diamine 17 can react with 14 through the amino group adjacent to $R^4$ to afford 9-anilinoacridines in which the substituent $R^4$ is ortho to the nitrogen attached to the acridine ring (e.g., 2, 5, 8 and 11). Finally, 9-anilinoacridines 3, 6, 9, and 12 can be synthesized by first condensing of 14 with nitroaniline 15, followed by reduction of the nitro group to an amino group. One can react 18 with an electrophilic source of acyl or alkoxycarbonyl groups, e.g., $YR^1$ (wherein "Y" is a leaving group displaced by the amino group), to afford derviatized 9-anilinoacridines 19. Y may be halo or RCOO—. Preferably, Y is chloro. In general, the ring substitution pattern of intermediates 13 or 14 can be retained in either 18 or 19.

Nucleophilic agents are known in the art and are described in the chemical texts and treatises referred to herein, and include reagents having electrons to share. Leaving groups are known in the art and are any stable species that can be detached from a molecule during a reaction (e.g., halides, triflates, alkoxides, alkylmercapto or amino). The chemicals used in the aforementioned methods can include, for example, solvents, reagents, catalysts, protecting group and deprotecting group reagents and the like. The methods described above can also additionally include steps, either before or after the steps described specifically herein, to add or remove suitable protecting groups in order to ultimately allow synthesis of the compound of the formulae described herein.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

To illustrate, the synthesis of exemplary compound 4 is delineated in Scheme 2. Exposure of compound 20 to thionyl chloride and a catalytic amount of dimethylformamide (DMF) resulted in the conversion of the 9-oxo and 4-carboxy groups to the corresponding chloro and acid chloride groups respectively. The intermediate dichloro compound was not isolated, but instead was treated with N,N-dimethylethylenediamine to afford compound 21, which now contains the desired amide at the 4-position of the acridine ring. Condensation of 21 with 3,5-diaminotoluene 22 provided 9-anilinoacridine 1, which in turn was converted to ethyl carbamate 4 with ethyl chloroformate.

SCHEME 2

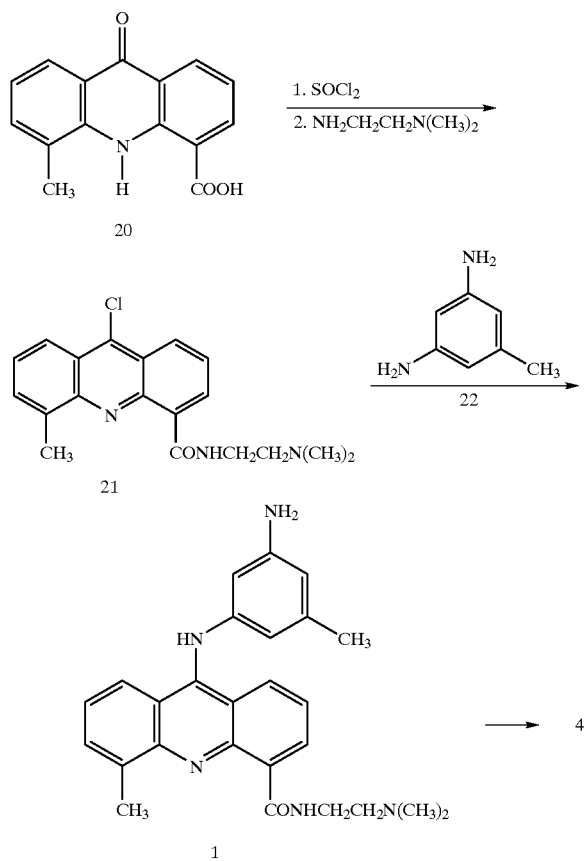

Also within the scope of this invention is a pharmaceutical composition that contains an effective amount of at least one 9-anilinoacridine compound of this invention and a pharmaceutically acceptable carrier. Further, this invention covers a method of administering an effective amount of one or more of such 9-anilinoacridine compounds to a cancer patient. "An effective amount" refers to the amount of an active 9-anilinoacridine compound that is required to confer a therapeutic effect on the treated subject. An effective amount may range from about 0.1 mg/Kg to about 500 mg/Kg, e.g., 1 mg/Kg to about 50 mg/Kg. Effective doses will vary, as recognized by those skilled in the art, depending on the types of diseases treated, route of administration, excipient usage, and the possibility of co-usage with other therapeutic treatment. Specific dosage and treatment regimens for any particular patient will depend upon a variety of factors, including the activity of the specific compound employed, the age, body weight, general health status. sex. diet, time of administration, rate of excretion, drug combination, the severity and course of the disease, condition or symptoms, the patient's disposition to the disease, condition or symptoms, and the judgment of the treating physician.

"Treating" refers to administering a compound described herein to a subject that prevents, cures, heals, alleviates, relieves, alters, remedies or ameliorates any primary phenomena (e.g., initiation, progression, metastasis) and/or secondary symptoms associated with the diseases delineated herein.

To practice the method of the present invention, a composition having one or more 9-anilinoacridne compounds can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active 9-anilinoacridine compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active indolizine compound. Examples of other carriers include colloidal silicon oxide, magnesium stearate, cellulose, sodium lauryl sulfate, and D&C Yellow #10.

The 9-anilinoacridines compounds of this invention can be preliminarily screened for their efficacy in treating cancers by one or more of the following in vitro assays and in vivo assays discussed below. Other methods will also apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of 5-[9-(4-dimethylaminoethylcarboxamido-5-methyl) acridinylamino]-m-toluidine hydrochloride (4'-CONHCH$_2$CH$_2$NMe$_2$-5 '-Me-AMT·3HCl or Compound 1·3HCl.

A mixture of known 5-methylacridin-9-one-4-carboxylic acid (6.0 g, 23.7 mmol) and thionyl chloride (15 mL) containing two drops of DMF was gently refluxed for 40 minutes. The mixture was concentrated under reduced pressure and the solid residue was added portionwise to a solution of N,N-dimethylethylenediamine (8.35 g, 94.8 mmol) and triethylamine (26.0 mL) in CHCl$_3$ (600 mL) at −10° C. After being stirred for 30 minutes, the solution was washed successively with 10% NaHCO$_3$ aqueous solution (100 mL×2) and water, dried over Na$_2$SO$_4$ and evaporated under reduced pressure to dryness to give crude 9-chloro-4-methylacridan-5-dimethylaminoethylcarboxamide (7.1 g, ca. 94%), which was used directly for the next reaction without further purification.

To a suspension of 3,5-diaminotoluene (3.0 g, 24.8 mmol) and 4-methylmorpholine (5.2 mL; 47.2 mmol) in EtOH (120 mL) was added dropwise a solution of crude 9-chloro-4-methylacridan-5-dimethylaininoethylcarboxamide (7.1 g; 22.6 mmol) in CHCl$_3$ (360 mL) in an ice-bath. After being stirred 1 hour at 0° C. for 1 hour, the temperature was allowed to rise to room temperature and was stirred continuously overnight. The reaction mixture was acidified to pH 2 by addition of ethanolic hydrochloride solution. The mixture was then evaporated to dryness in vacuo and the solid residue was dissolved in mixture of hot MeOH (600 mL)/CHCl$_3$ (200 mL), treated with active charcol, and filtered through a pad of celite. The filtrate was concentrated under reduced pressure and the solid product was crystallized from EtOH to give 5-[9-(4-dimethylaminoethylcarboxamido-5-methyl)acridinylamino]-m-toluidine (4'-CONHCH$_2$CH$_2$NMe$_2$-5'-AMT); 6.4 g (58%): mp 239–240° C.; $^1$H NMR (DMSO-d$_6$) δ 2.26 (3H, s, ArMe), 2.73 (3H, s, ArMe), 2.87 (6H, s, NMe$_2$), 3.44 (2H, t, J=5.5 Hz, CH$_2$), 3.83 (2H, t, J=5.5 Hz, CH$_2$), 6.92 (1H, m, ArH), 6.98 (1H, m, ArH), 7.07 (1H, m, ArH), 7.42 (1H, m, ArH), 7.59 (1H, m, ArH), 7.94 (1H, m, ArH), 8.21 (1H, m, ArH), 8.58 (1H, m, ArH), 8.92 (1H, m, ArH), 10.04, 10.89 and 11.96 (each 1H, brs, exchangeable, NH). Calculated for C$_{26}$H$_{29}$N$_5$O.3HCl.3H$_2$O: C, 52.84; H, 6.48; N, 11.85. Found: C, 52.91.H, 6.47; N, 11.46.

EXAMPLE 2

Preparation of 3-[9-(4-dimethylaminoethylcarboxamido-5-methyl) acridinylamino)-p-toluidine hydrochloride (4'-CONHCH$_2$CH$_2$NMe$_2$-5'-Me-APT.3HCl) or Compound 2.3HCl.

Following the same procedure as that for the synthesis of 4'-CONHCH$_2$CH$_2$NMe$_2$-5'-Me-AMT.3 HCl, (4'-CONHCH$_2$CH$_2$NMe$_2$-5'-Me-APT 3HCl) was prepared from 2,4-diaminotoluene (2.44 g, 20.0 mmol), crude 9-chloro-4-methylacridan-5-dimethylaminoethylcarboxamide (6.84. g, 20.0 mmol) and 4-methylmorpholine (4.4. mL; 40.0. mmol): yield 5.29 g (57%): mp 228–229° C.; $^1$H NMR (DMSO-d$_6$) δ 2.32 (3H, s, ArMe), 2.72 (3H, s, ArMe), 2.87 (6H, s, NMe$_2$), 3.42 (2H, d, J=4.3 Hz, CH$_2$), 3.83 (2H, d, J=4.3 Hz, CH$_2$), 6.95 (1H, m, J=5.5 Hz, ArH), 7.25 (1H, s, ArH), 7.26 (1H, d, J=5.5 Hz, ArH),7.40 (1H, m, ArH), 7.56 (1H, m, ArH), 7.92 (1H, m, ArH), 8.21 (1H, m, ArH), 8.58 (1H, m, ArH), 8.90 (1H, m, ArH), 10.04, 10.89 and 11.96 (each 1H, brs, exchangeable, NH). Calculated for C$_{26}$H$_{29}$N$_5$O.3HCl.3H$_2$O: C, 52.84; H, 6.48; N, 11.85. Found: C, 53.07; H, 6.50; N, 11.42.

EXAMPLE 3

Preparation of 4-[9-(4-dimethylaminoethylcarboxamido-5-methyl) acridinylamino]-2-nitrotoluene Following the same procedure as that for the synthesis of 4'-CONHCH$_2$CH$_2$NMe$_2$-5'-Me-AMT.3 HCl with the modification of using concentrated HCl as the catalyst for condensation in place of of 4-methylmorpholine, 4-[9-(4-dimethylaminoethylcarboxamido-5-methyl)-acridinylamino]-2-nitrotoluene was prepared from 4-amino-2-nitrotoluene (3.38 g, 22 mmol), crude 9-chloro-4-methylacridan-5-dimethylaminoethylcarboxamide (6.83 g, 20.0 mmol) and a catalytic amount of concentrated HCl (0.5 mL): yield 6.25 g (59%): mp 241–242° C.; NMR (DMSO-d$_6$) δ 2.56 and 2.74 (each 3H, s, Me), 2.87 and 2.88 (each 3H, s, NMe$_2$), 3.42 (2H, m, CH$_2$), 3.85 (2H, m, CH$_2$), 7.43–7.45 (1H, m, ArH), 7.59–7.61 (3H, m, ArH), 7.94 (1H, m, ArH), 8.10 (1H, m, ArH), 8.22 (1H, m, ArH), 8.63 (1H, m, ArH), 8.90 (1H, m, ArH), 10.06 and 10.78 (each 1H, brs, NH). Calculated for C$_{26}$H$_{27}$N$_5$O$_3$.2HCl.1.5H$_2$O: C, 56.02; H, 5.79; N, 12.56. Found: C, 56.31; H, 5.90; N, 12.72.

EXAMPLE 4

Preparation of 5-[9-(4-dimethylaminoethylcarboxamido-5-methyl) acridinylamino)-p-toluidine hydrochloride (4'-CONHCH$_2$CH$_2$NMe$_2$-5'-Me-AOT.3HCl) or Compound 3.3HCl).

A mixture of 4-[9-(4-dimethylaminoethylcarboxamido-5-methyl)acridinylamino]-2-nitrotoluene (3.0 g, 6.6 mmol) and 10% Pd/C (3.8 g) in DMF (12 mL) and MeOH (120 mL) containing conc. HCl (12 mL) was hydrogenated at 50 psi for 5 hours. The mixture was filtered through a pad of celite, washed with DMF (10 mL). The combined filtrate and washing were concentrated under reduced pressure and the residue was crystallized from EtOH to give 4'-CONHCH$_2$CH$_2$NMe$_2$-5'-Me-APT.3HCl; 2.43 g (86%): mp 245–246° C.; $^1$H NMR (DMSO-d$_6$) δ 2.34 and 2.75 (each 3H, s, Me), 2.86 and 2.87 (each 3H, s, NMe$_2$), 3.43 and 3.85 (each 2H, m, CH$_2$), 7.02 (1H, m, ArH), 7.27–7.29 (1H, m, ArH), 7.39–7.40 (2H, m, ArH), 7.57 (1H, m, ArH), 7.93 (1H, m, ArH), 8.21 (1H, m, ArH), 8.59 (1H, m, ArH), 8.92 (1H, m, ArH), 9.07 (2H, brs, NH2), 10.09, 10.89, and 11.90 (each 1H, brs, NH). Calculated for C$_{26}$H$_{29}$N$_5$O.3HCl.2H$_2$O: C, 54.50; H, 6.33; N, 12.22. Found: C, 54.71; H, 6.42; N, 12.40.

EXAMPLE 5

Preparation of {3-[4-(2-dimethylaminoethylcarbamoyl)-5-methylacridin-9-ylamino]-5-methylphenyl}-carbamic acid ethyl ester (Compound 4).

Ethyl chloroformate (0.23 mL; 2.4 mmol) was added dropwise to a suspension of 4'-CONHCH$_2$CH$_2$NMe$_2$-5'-Me- AMT (928 mg; 2.0 mmol) in dry DMF (20 mL) containing pyridine (0.32 mL, 4.0 mol) at −10 to 0° C. After being stirred for 2 hours, the mixture was evaporated in vacuo to dryness. The residue was treated with 1N HCl/EtOH in an ice-bath to pH 2 and evaporated under reduced pressure to dryness. The solid residue was recrystallized from EtOH to give {3-[4-(2-dimethylamino-ethylcarbamoyl)-5-methylacridin-9-ylamino]-5-methyl-phenyl}-carbamic acid ethyl ester: yield 905 mg (85%); mp 263–264° C.; $^1$H NMR (DMSO-$d_6$) δ 1.23 (3H, t, J=7.0 Hz, Me), 2.26 (3H, s, Me), 2.73 (3H, s, Me), 2.91 (6H, s, NMe$_2$), 3.43 (2H, d, J=5.3 Hz, CH$_2$), 3.82 (2H, J=5.3 Hz, CH$_2$), 4.10 (2H, q, J=6.9 Hz, CH$_2$), 6.86 (1H, s, ArH), 7.29 (1H, s, ArH), 7.42 (1H, m, ArH), 7.46 (1H, s, ArH), 7.59 (1H, m, ArH), 7.93 (1H, m, ArH), 8.12 (1H, m, ArH), 8.47 (1H, m, ArH), 8.72 (1H, m, ArH), 9.78 and 9.87 (each 1H, brs, 2×NH).

Calculated for $C_{29}H_{33}N_5O$.$_3$2HCl.1.3H$_2$O: C, 58.39:H, 6.63; N, 11.74. Found C, 58.25; H, 6,20; N, 11.34.

EXAMPLE 6

{3-[4-(2-dimethylamino ethylcarbamoyl)-5-methyl-acridin-9-ylamino]-2-methyl-phenyl}-carbamic acid ethyl ester (Compound 5).

Following the same procedure as that for the synthesis of compound 4, compound 5 was prepared from 4'-CONHCH$_2$CH$_2$NMe$_2$5'-Me-APT.3HCl (or Compound 2.3HCl).(930 mg, 2.0 mmol) and ethyl chloroformate (0.23 mL, 2.4 mmol): yield 858 mg (80%); mp 182–183° C.; $^1$H NMR (DMSO-$d_6$) δ 1.21 (3H, t, J=7.0 Hz, Me), 2.29 (3H, s, ArMe), 2.73 (3H, s, ArMe), 2.87 (6H, s, NMe$_2$), 3.41 (2H, brs, Hz, CH$_2$), 3.82 (2H, brs, CH$_2$), 4.08 (2H, q, J=7.0 Hz, CH$_2$), 7.09 (1H, m, ArH), 7.31 (1H, m,ArH), 7.40 (1H, m, ArH), 7.57 (1H, m, ArH), 7.62 (1H, s, ArH), 7.93 (1H, m, ArH), 8.21 (1H, m, ArH), 8.88 (1H, m, ArH), 9.06, 10.05, and 10.81 (each, 1H, brs, 3×NH). Calculated for $C_{29}H_{33}N_5O_3$-.3HCl.2H$_2$O: C, 63.01; H, 6.61; N, 11.49. Found: C, 65.23; H, 6.53; N, 11.71.

EXAMPLE 7

5-[4-(2-dimethylaminoethylcarbamoyl)-5-methylacridin-9-ylamino]-2-methyl-phenyl]-carbamic acid ethyl ester (Compound 6).

Following the same procedure as that for the synthesis of compound 4, compound 6 was prepared from 4'-CONHCH$_2$CH$_2$NMe$_2$-5'-Me-AOT2.3HCl (or Compound 33HCl) (1.10 mg, 2.66 mmol) and ethyl chloroformate (0.30 mL, 3.19 mmol): yield 858 mg (80%); mp 131–132° C.;

$^1$H NMR (DMSO-$d_6$) δ 1.21 (3H, t, J=7.0 Hz, Me), 2.29 (3H, s, ArMe), 2.73 (3H, s, ArMe), 2.87 (6H, s, NMe$_2$), 3.41 and 3.82 (each 2H, brs, CH$_2$), 4.08 (2H, q, J=7.0 Hz, CH$_2$), 7.09 (1H, m, ArH), 7.31-7.33 (1H, m, ArH), 7.38–7.42 (1H, m, ArH), 7.54–7.61 (2H, m, 2×ArH), 7.92–7.94 (1H, m, ArH), 8.18–8.20 (1H, m, ArH), 8.54–8.8.57 (1H, m, ArH), 8.86 (1H, m, ArH), 9.02 (1H, brs, NH), 10.07(2H, brs, 2×NH). Anal. ($C_{29}H_{33}N_5O_3$3HCl.3H$_2$O)C, H, N.

EXAMPLE 8

Preparation of 5-[9-(4-methylacridinylamino]-m-toluidine hydrochloride (4'-Me-AMT.HCl or Compound.7 HCl)

Following the same procedure as that for the synthesis of compound 1,4'-Me-AMT.HCl was synthesized from 3,5-diaminotoluene hydrochloride (3.90 g; 0.20 mmol), 4-methyl-9-chloroacridine (4.55 g; 0.02 mmol) and 4-methylmorpholine (4.4 mL; 40.mmol): yield 4.27 g (61%); mp>290° C.; $^1$H NMR (DMSO-$d_6$) δ 2.27 (3H, s, Me), 2.84 (3H, s, ArMe), 7.07 (2H, m, ArH), 7.18 (1H, m, ArH), 7.39 (1H, m, ArH), 7.48 (1H, m, ArH), 7,87 (1H, m, ArH), 8.02 (1H, m, ArH), 8.23 (1H, m, ArH), 8.29 (1H, m, ArH), 8.68 (1H, m, ArH), 11.40 and 12.60 (each 1H, brs, 2×NH). Calculated for $C_{21}H_{19}N_3$-HCl 0.13H$_2$O: C, 71.63; H, 5.80; N, 11.93. Found: C, 71.93; H, 5.89; N, 11.54.

EXAMPLE 9

Preparation of 5-[9-(4-Methyl)acridinylamino]- p-toluidine hydrochloride (4'-Me-APT.HCl or Compound.8 HCl).

Following the same procedure as that for the synthesis of compound 1,4'-Me-APT.HCl was synthesized from 4-diaminotoluene (2.44 g, 20.0 mmol), 9-chloro4-methylacridine (4.55 g, 20 mmol) and 4-methylmorpholine (4.4 mL; 40 mmol): yield 6.16 g (88%); mp>280° C.; $^1$H NMR (DMSO-$d_6$) δ 2.37 (3H, s, ArMe), 2.83 (3H, s, ArMe), 7.08 (1H, m, ArR), 7.30 (1H, m, ArH), 7.37–7.48 (3H, m, ArH), 7.86 (1H, m, ArH), 8.01 (1H, m, ArH), 8.25 (2H, m, 2×ArH), 8.61 (1H, m, ArH), 11.71 and 12.96 (each 1H, brs, exchangeable, NH). Calculated for $C_{21}H_{19}N_3$.HCl 0.25H$_2$O: C, 70.38; H, 5.77; N, 11.72. Found: C, 70.98; H, 6.06; N, 11.42.

EXAMPLE 10

Preparation of 4-(9-acridinylamino)-2-nitrotoluene

Following the same procedure as that for the synthesis of 4-[9-(4-dimethylaminoethyl-carboxamido-5-methyl)acridinylamino]-2-nitrotoluene, 4-(9-acridinylamino)-2-nitrotoluene was synthesized from 4-amino-2-nitrotoluene (3.35 g; 22 mmol) and 9-chloroacridine (4.27 g; 20 mmol): yield 6.60 g (90%); mp>280° C.; $^1$H NMR (DMSO-$d_6$) $^1$H NMR (DMSO-$d_6$) δ 2.57 (3H, s, Me), 7.50–7.61 (4H, m, ArH), 8.02–8.05 (2H, m, ArH), 8.00 (1H, m, ArH), 8.16–8.18 (1H, m, ArH), 8.30–8.34 (1H, m, ArH), 11.70 (1H, brs, NH). Calculated for $C_{20}H_{15}N_3O_2$.HCl.1.25H$_2$O: C, 61.85; H, 4.80; N, 10.82. Found: C, 61.57; H, 4.65; N, 10.59.

EXAMPLE 11

Preparation of 4-[9-(4-methyl)acridinylamino]-2-nitrotoluene

Following the same procedure as that for the synthesis of 4-(9-(4-dimethylaminoethyl-carboxamido-5-methyl) acridinylamino]-2-nitrotoluene, 4-[9-(4-methyl)acridinylamino]-2-nitrotoluene was prepared from 9-chloro-4-methylacridine (4.57 g, 20 mmol) and 4-amino-2-nitrotoluene (3.35 g, 22 mmol): yield 6.65 g (86%); mp>280° C.; $^1$H NMR (DMSO-$d_6$) δ 2.60 (3H, s, Me), 2.85 (3H, s, Me), 7.41–7.45 (1H, m, ArH), 7.50–7.58 (4H, m, ArH), 7.89–7.91 (1H, m, ArH), 8.02–8.08 (2H, m, ArH), 8.21–8.24 (1H, m, ArH), 8.30–8.33 (1H, m, ArH), 8.59–8.61 (1H, m,ArH), 11.75 (H, brs, NH). Calculated for $C_{21}H_{17}N_3O_2$.HCl.0.25H$_2$O: C, 65.62; H, 4.85; N, 10.93. Found: C, 65.88; H, 4.86; N, 10.63.

EXAMPLE 12

Preparation of 4-[9-(4-methyl)acridinylamino)-o-toluidine (4'-Me-AOT.HCl or compound 9)

Following the same procedure as that for the synthesis of 4'-CONHCH$_2$CH$_2$NMe$_2$-5'-Me-AOT (or Compound 3), 4-[9-(4-methyl)acridinylamino)-o-toluidine (4'-Me-AOT.HCl or compound 9) was prepared from 4-[9-(4-methyl)acridinylamino]-2-nitrotoluene (3.09 g, 9.0 mmol): yield, 1.64 g, 58%. >280° C.; $^1$H NMR (DMSO-d$_6$) δ 2.36 and 2.78 (each 3H, s, Me), 7.01 (1H, m, ArH), 7.28–7.30 (1H, m, ArH), 7.35 (1H, m, ArH), 7.40–7.44 (1H, m, ArH), 7.42–7.44 (1H, m, ArH), 7.48–7.52 (1H, m, ArH), 7.89–7.91 (1H, m, ArH), 8.01–8.05 (1H, m, ArH), 8.27–8.32 (2H, m, ArH), 8.63–8.63 (1H, m, ArH), 11.71 (1H, brs, NH). Calculated for $C_{21}HR_9N_3$-2HCl.0.3H$_2$O: C, 64.39; H, 5.48; N, 10.72. Found: C, 64.18; H, 5.72; N, 10.59.

EXAMPLE 13

Preparation of 5-(9-acridinylamino)-m-toluidine (AMR.HCl or Compound 10.HCl).

A solution of 9-chloroacridine (4.27 g; 20 mmol) in CHCl$_3$ (20 mL) was added dropwise to a mixture of 3,5-diaminotoluene hydrochloride (3.90 g; 20 mmol) and 4-methylmorpholine (4.4 mL; 40.mmol) in MeOH (50 mL) at –10–5° C. After being stirred for 1 hour, the temperature was raised to room temperature and was continuously stirred for additional 3 hours. The orange precipitated product was collected by filtration, washed with EtOH and recrystallized from MeOH/CHCl$_3$ to give 3-(9-acridinylamino)- (p)-toluidine hydrochloride, 4.85 g (85%): mp >280° C. (dec); $^1$H NMR (DMSO-d$_6$) δ 2.26 (3H, s, ArMe), 6.90 (2H, s, ArH), 6.95 (1H, s, ArH), 7.48 (2H, m, 2×ArH), 8.02 (2H, m, 2×ArH), 8.16 (2H, m, 2×ArH), 8.33 (2H, m, 2×ArH), 10.05 and 11.53 (each 1H, brs, exchangeable, NH). Calculated for $C_{20}H_{17}N_3$.2HCl.1.75 H$_2$O: C, 59.48; H, 5.62; N, 10.41. Found: C, 59.58; H, 5.61; N, 10.02.

EXAMPLE 14

Preparation of 4-(9-Acridinylamino)-p-toluidine (APT.HCl or Compound 11 HCl).

Following the same procedure as that for the synthesis of AMT.HCl, APT.HCl or compound 11 was synthesized from 2,4-diaminotoluene (2.44 g, 20.0 mmol), 9-chloroacridine (4.27 g; 20.0 mmol) and 4-methylmorpholine (4.4 mL; 40 mmol): yield 5.78 g (86%): mp>280° C.; $^1$H NMR (DMSO-d$_6$) δ 2.38 (3H, s, ArMe), 7.12 (1H, m, ArH), 7.32 (1H, m, ArH), 7.38 (1H, m, ArH), 7.47 (2H, m, 2×ArH), 8.01 (2H, m, 2×ArH), 8.18 (2H, m, 2×ArH), 8.30 (2H, m, 2×ArH), 11.49 (1H, brs, exchangeable, NH). Calculated for $C_{20}H_{17}N_3$.HCl.2H$_2$O: C, 61.54; H, 5.42; N, 10.07. Found: C, 61.76; H, 5.75; N, 10.38.

EXAMPLE 15

Preparation of 4-(9-acridinylamino)-atoluidine (AOT.HCl or compound 12)

Following the same procedure as that for the synthesis of 4'-CONHCH$_2$CH$_2$NMe$_2$-5'-Me-AOT (or Compound 3), 4-(9-acridinylamino)-o-toluidine (AOT.HCl or compound 12) was prepared from 4-(9-acridinylamino)-2-nitrotoluene (3.0 g, 9.1 mmol): yield 2.0 g (73%); mp 256–257° C.; $^1$H NMR (DMSO-d$_6$) δ 2.29 (3H, s, Me), 6.92 (1H, m, ArH), 7.23 (1H, m, ArH), 7.45–7.49 (2H, m, ArH), 7.99–8.03 (2H, m, ArH), 8.10–8.12 (2H, m, ArH), 8.29–8.31 (2H, m, ArH), 11.56 (3H, brs, NH). Calculated for $C_{20}H_{17}N_3O_2$.HCl.4H$_2$O: C, 58.90; H, 6.42; N, 10.30. Found: C, 58.96; H, 6.13; N, 10.03.

EXAMPLE 16

Inhibition of Human Tumor Cell Growth in Culture

Cytotoxicity Assays. The effects of the compounds on cell growth were determined in all human tumor cells (i.e. colon HT-29, nasopharyngeal carcinoma HONE-1 and BM-1, hepatoma Hepa-G2, breast carcinoma MX-1, gastric carcinoma TSGH, brain tumor DBTRG, oral carcinoma KB, breast carcinoma MCF-7 and MX-1, and T-cell acute lymphocytic leukemia CCRF-CEM), in a 72 h incubation, by XTT-tetrazolium assay, as described by Scudiero et al. (*Cancer Res.* 1988, 48, 4827–4833). After the addition of phenazine methosulfate-XTT solution at 37° C. for 6 h, absorbance at 450 and 630 nm was detected on a microplate reader (EL 340; Bio-Tek Instruments Inc., Winooski, Vt.). Six to seven concentrations of each compound were used. The IC$_{50}$ and dose-effect relationships of the compounds for antitumor activity were calculated by a median-effect plot (Chou et al. *Adv. Enzyme Regul.* 1984, 22, 27–55) using a computer program on an IBM-PC workstation (Chou et al. *Dose-Effect Analysis with Microcomputers: Quantitation of ED$_{50}$, LD$_{50}$, Synergism, Antagonism, Low-Dose Risk, Receptor-Ligands Binding and Enzyme Kinetics*; Biosoft: Cambridge, U.K., 1987).

Compounds 1, 2, 3, 4, 5 and 6 were tested on five human tumor cell lines. Unexpectedly, for at least one cell line all compounds exhibited IC$_{50}$ values that were lower than those of tested known 9-anilinoacridine antitumor compounds. The largest difference observed was an 18 fold difference between compound 2 and one of the tested known compounds.

EXAMPLE 17

Growth Inhibition of CCRF-CEM Human Lymphoblastic Leukemic Cells and its Drug-Resistant Sublines Cytotoxicity Assays. The effects of the compounds on cell growth were determined in CCRF-CEM human lymphoblastic leukemic cells and its drug-resistant sublines in a 72 h incubation, by XTT-tetrazolium assay, as described by Scudiero et al. (*Cancer Res.* 1988, 48, 4827–4833). After the addition of phenazine methosulfate-XTT solution at 37° C. for 6 h, absorbance at 450 and 630 nm was detected on a microplate reader (EL 340; Bio-Tek Instruments Inc., Winooski, Vt.). Six to seven concentrations of each compound were used. The IC$_{50}$ and dose-effect relationships of the compounds for antitumor activity were calculated by a median-effect plot (Chou et al. *Adv. Enzyme Regul.* 1984, 22, 27–55) using a computer program on an IBM-PC workstation (Chou et al. *Dose-Effect Analysis with Microcomputers: Quantitation of ED$_{50}$, LD$_{50}$, Synergism, Antagonism, Low-Dose Risk, Receptor-Ligands Binding and Enzyme Kinetics*; Biosoft: Cambridge, U.K., 1987).

Compounds 1 and 2 were tested. Unexpectedly, both 1 and 2 (as the trihydrochloride salt or free amine compounds) exhibited IC$_{50}$ values that were lower than tested known 9-anilinoacridine compounds. Both compounds 1 and 2 are not cross-resistant with vinblastine or taxol.

EXAMPLE 18

Chemotherapeutic efficacy of compounds on the inhibition of nude mice bearing human breast tumor MX-1 xenograft In vivo assay. Athymic nude mice bearing the nu/nu gene were used for human breast tumor MX-1 xenograft. Outbred Swiss-background mice were obtained from Charies River Breeding Laboratories. Male mice 8 weeks old or older weighing 22 g or more were used for most experiments. Drug was administrated via the tail vein by i.v. injection. Tumor volumes were assessed by measuring length x width x height (or width) by using caliper. Vehicle used was 20 μl DMSO in 180 μl saline. All animal studies were conducted in accordance with the guidelines of the National Institutes of Health Guide for the Care and Use of Animals and the protocol approved by the Memorial Sloan-Kettering Cancer Center's Institutional Animal Care and Use Committee.

Compounds 1 and 2 were tested. Both compounds, at dosages of 10 mg/Kg or higher, were effective in reducing tumor volume by about 80% and had very low toxicity to the host. These results were comparable or superior to known tested 9-anilinoacridine compounds.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A compound of the following Formula (I)

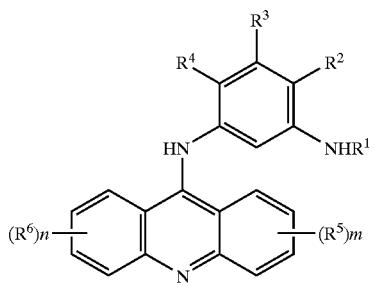

(I)

wherein, $R^1$ is hydrogen, $COR^a$, or $COOR^a$;

each of $R^2$, $R^3$ and $R^6$ is, independently, hydrogen, $C_1$–$C_{10}$ alkyl, or $OR^b$, with the proviso that $R^2$, $R^3$ and $R^4$ cannot all be hydrogen;

each of $R^5$ and $R^6$ is, independently, hydrogen, $C_1$–$C_6$ alkyl, $OR^c$, nitro, halo, $N(R^c)_2$, $NH(CH_2)_pN(R^c)_2$, $(CH_2)_qOH$, $(CH_2)_qX$, $CONHR^c$, $CONH(CH_2)_pN(R^c)_2$, $SO_3R^c$, or $SO_2R^c$ with the proviso that when $R^1$ is hydrogen and $R^4$ is $CH_3$, $R^5$ and $R^6$ cannot both be hydrogen and furthermore, both m & n can not be 0 simultaneously; and each of m and n, is independently, 0–4;

in which $R^a$ is aryl, or $C_1$–$C_{10}$ alkyl, optionally substituted with oxo; $R^b$ is $C_1$–$C_{10}$ alkyl; $R^c$ is hydrogen or $C_1$–$C_{10}$ alkyl; p is 1–5; and q is 1–3.

2. The compound of claim 1, wherein one of $R^2$, $R^3$ and $R^4$ is $C_1$–$C_6$ alkyl or $OR^b$ and one of $R^2$, $R^3$ and $R^4$ is hydrogen.

3. The compound of claim 2, wherein $R^1$ is hydrogen.

4. The compound of claim 2, wherein $R^1$ is $COR^a$ or $COOR^a$.

5. The compound of claim 4, wherein $R^a$ is $C_1$–$C_4$ alkyl, optionally substituted with oxo.

6. The compound of claim 2, wherein each of $R^5$ and $R^6$ is independently, hydrogen, $C_1$–$C_6$ alkyl, $OR^c$ or $CONHR^c$, or $CONH(CH_2)_pN(R^c)_2$, and each of m and n is, independently, 1.

7. The compound of claim 6, wherein $R^c$ is $C_1$–$C_4$ alkyl and p is 2.

8. The compound of claim 2, wherein one of $R^2$, $R^3$ and $R^4$ is $C_1$–$C_4$ alkyl or $OR^b$, $R^b$ being $C_1$–$C_4$ alkyl.

9. The compound of claim 8, wherein $R^1$ is $COR^a$ or $COOR^a$, $R^a$ being $C_1$–$C_4$ alkyl, optionally substituted with oxo.

10. The compound of claim 8, wherein $R^1$ is H.

11. The compound of claim 8, wherein $R^5$ and $R^6$ are each independently hydrogen, $C_1$–$C_6$ alkyl, $OR^c$ or $CONHR^c$, or $CONH(CH_2)_pN(R^c)_2$; and each of m and n is, independently, 1.

12. The compound of claim 11, wherein $R^c$ is $C_1$–$C_4$ alkyl and p is 2.

13. The compound of claim 2, wherein one of $R^2$, $R^3$ and $R^4$ is $CH_3$ or $OCH_3$.

14. The compound of claim 13, wherein $R^1$ is $COR^a$ or $COOR^a$.

15. The compound of claim 14, wherein $R^a$ is $C_1$–$C_4$ alkyl, optionally substituted with oxo.

16. The compound of claim 15, wherein $R^1$ is $COCH_2CH_2COCH_3$ or $COOCH_2CH_3$.

17. The compound of claim 16, wherein $R^5$ and $R^6$ are each independently hydrogen, $C_1$–$C_6$ alkyl, $OR^c$, $CONHR^c$, or $CONH(CH_2)_pN(R^c)_2$; and each of m and n is, independently, 1.

18. The compound of claim 17, wherein $R^c$ is $C_1$–$C_4$ alkyl and p is 2.

19. The compound of claim 18, wherein $R^5$ is $CONH(CH_2)_2N(CH_3)_2$ and $R^6$ is $CH_3$.

20. The compound of claim 19, wherein $R^5$ and $R^6$ are at the C-4 and C-5 positions of the acridine ring, respectively.

21. The compound of claim 20, wherein the compound is {3-[4-(2-dimethylamino-ethylcarbamoyl)-5-methyl-acridin-9-ylamino]-5-methyl-phenyl}-carbamic acid ethyl ester, or {3-[4-(2-dimethylamino-ethylcarbamoyl)-5-methyl-acridin-9-ylamino]-4-methyl-phenyl}-carbamic acid ethyl ester.

22. The compound of claim 13, wherein $R^1$ is hydrogen.

23. The compound of claim 22, wherein $R^5$ and $R^6$ are each independently hydrogen, $C_1$–$C_6$ alkyl, $OR^cCONHR^c$, or $CONH(CH_2)_pN(R^c)_2$, and each of m and n is, independently, 1.

24. The compound of claim 23, wherein $R^c$ is $C_1$–$C_4$ alkyl and p is 2.

25. The compound of claim 24, wherein $R^5$ is $CONH(CH_2)_2N(CH_3)_2$ and $R^6$ is $CH_3$.

26. The compound of claim 25, wherein $R^5$ and $R^6$ are at the C-4 and C-5 positions of the acridine ring, respectively.

27. The compound of claim 26, wherein the compound is [9-(1-amino-5-methyl-phenyl)amino]-5-methyl-acridine-4-carboxylic acid (2-dimethylamino-ethyl)-amide or [9-(5-amino-2-methyl-phenyl)amino]-5-methyl-acridine-4-carboxylic acid (2-dimethylamino-ethyl)-amide.

28. A pharmaceutical composition comprising a compound of Formula (I):

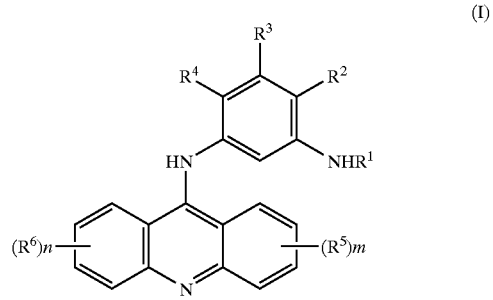

(I)

wherein, $R^1$ is hydrogen, $COR^a$, or $COOR^a$;

each of $R^2$, $R^3$ and $R^4$ is, independently, hydrogen, $C_1$–$C_{10}$ alkyl, or $OR^b$, with the proviso that $R^2$, $R^3$ and $R^4$ cannot all be hydrogen;

each of $R^5$ and $R^6$ is, independently, hydrogen, $C_1$–$C_6$ alkyl, $OR^c$, nitro, halo, $N(R^c)_2$, $NH(CH_2)_pN(R^c)_2$, $(CH_2)_qOH$, $(CH_2)_qX$, $CONHR^c$, $CONH(CH_2)_pN(R^c)_2$, $SO_3R^c$, or $SO_2R^c$ with the proviso that when $R^1$ is hydrogen and $R^4$ is $CH_3$, $R^5$ and $R^6$ cannot both be hydrogen; and furthermore, both m and n can not be 0 simultaneously and each of m and n, is independently, 0–4;

in which $R^a$ is aryl, or $C_1$–$C_{10}$ alkyl, optionally substituted with oxo; $R^b$ is $C_1$–$C_{10}$ alkyl; $R^c$ is hydrogen or $C_1$–$C_{10}$ alkyl; p is 1–5; and q is 1–3; and a pharmaceutically acceptable salt or carrier.

29. The composition of claim 28, wherein one of $R^2$, $R^3$ and $R^4$ is $C_1$–$C_6$ alkyl or $OR^b$ and one of $R^2$, $R^3$ and $R^4$ is hydrogen; each of $R^5$ and $R^6$ is independently, hydrogen, $C_1$–$C_6$ alkyl, $OR^c$ or $CONHR^c$, or $CONH(CH_2)_pN(R^c)_2$; each of m and n is, independently 1; $R^c$ is $C_1$–$C_4$ alkyl: and p is 2.

30. The composition of claim 28, wherein one of $R^2$, $R^3$ and $R^4$ is $CH_3$ or $OCH_3$ and one of $R^2$, $R^3$ and $R^4$ is hydrogen.

31. The composition of claim 28, wherein the compound is {3-[4-(2-dimethylamino-ethylcarbamoyl)-5-methyl-acridin-9-ylamino]-5-methyl-phenyl}-carbamic acid ethyl ester, or {3-[4-(2-dimethylamino-ethylcarbamoyl)-5-methyl-acridin-9-ylamino]-4-methyl-phenyl}-carbamic acid ethyl ester.

32. The composition of claim 28, wherein the compound is a [9-(1-amino-5-methyl-phenyl)amino]-5-methyl-acridine-4-carboxylic acid (2-dimethylamino-ethyl)-amide or [9-(5-amino-2-methyl-phenyl)amino]-5-methyl-acridine-4-carboxylic acid (2-dimethylamino-ethyl)-amide.

33. A method of treating cancer, comprising administering to a subject in need thereof an effective amount of the compound of Formula (I):

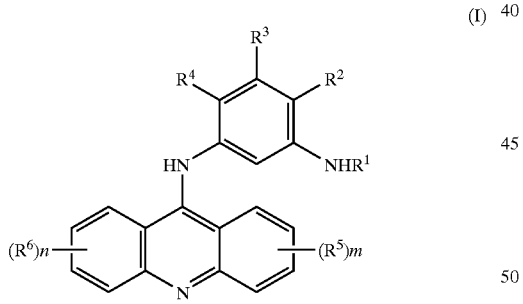

wherein, $R^1$ is hydrogen, $COR^a$, or $COOR^a$;

each of $R^2$, $R^3$ and $R^4$ is, independently, hydrogen, $C_1$–$C_{10}$ alkyl, or $OR^b$, with the proviso that $R^2$, $R^3$ and $R^4$ cannot all be hydrogen;

each of $R^5$ and $R^6$ is, independently, hydrogen, $C_1$–$C_6$ alkyl, $OR^c$, nitro, halo, $N(R^c)_2$, $NH(CH_2)_pN(R^c)_2$, $(CH_2)_qOH$, $(CH_2)_qX$, $CONHR^c$, $CONH(CH_2)_pN(R^c)_2$, $SO_3R^c$, or $SO_2R^c$ with the proviso that when $R^1$ is hydrogen and $R^4$ is $CH_3$, $R^5$ and $R^6$ cannot both be hydrogen; and furthermore, both m and n can not be 0 simultaneously and each of m and n, is independently, 0–4;

in which $R^a$ is aryl, or $C_1$–$C_{10}$ alkyl, optionally substituted with oxo; $R^b$ is $C_1$–$C_{10}$ alkyl $R^c$ is hydrogen or $C_1$–$C_{10}$ alkyl; p is 1–5; and q is 1–3.

34. The method of claim 33, wherein the cancer is colon cancer, stomach cancer, brain cancer, breast cancer, or leukemia.

35. A method for synthesizing a compound of Formula (II):

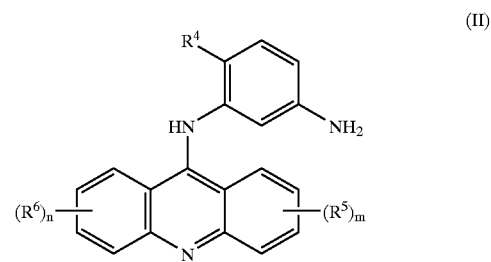

the method comprising: contacting a compound of Formula (III):

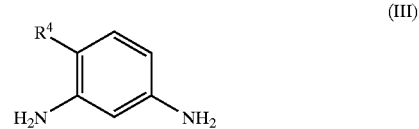

with a compound of Formula (IV):

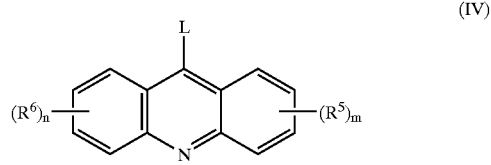

to form a compound of Formula (II), wherein:

$R^4$ is $C_1$–$C_{10}$ alkyl or $OR^b$;

each of $R^5$ and $R^6$ is, independently, hydrogen, $C_1$–$C_6$ alkyl, $OR^c$, nitro, halo, $N(R^c)_2$, $NH(CH_2)_pN(R^c)_2$, $(CH_2)_qOH$, $(CH_2)_qX$, $CONHR^c$, $CONH(CH_2)_pN(R^c)_2$, $SO_3R^c$, or $SO_2R^c$; and each of m and n, is independently, 0–4;

in which $R^a$ is aryl, or $C_1$–$C_{10}$ alkyl, optionally substituted with oxo; $R^b$ is $C_1$–$C_{10}$ alkyl; $R^c$ is hydrogen or $C_1$–$C_{10}$ alkyl; p is 1–5; q is 1–3;

L is halo, $OSO_2R^7$, or $OR^7$; and $R^7$ is alkyl, haloalkyl, or aryl optionally substituted with halo or nitro.

* * * * *